(12) United States Patent
Rejndrup et al.

(10) Patent No.: US 11,688,496 B2
(45) Date of Patent: Jun. 27, 2023

(54) HEALTH INFORMATION EXCHANGE SYSTEM

(71) Applicant: Anju Software, Inc., Tempe, AZ (US)

(72) Inventors: Kim Rejndrup, Tempe, AZ (US); Keith Howells, Tempe, AZ (US)

(73) Assignee: Anju Software, Inc., Tempe, AZ (US)

( * ) Notice: Subject to any disclaimer, the term of this patent is extended or adjusted under 35 U.S.C. 154(b) by 73 days.

(21) Appl. No.: 16/840,123

(22) Filed: Apr. 3, 2020

(65) Prior Publication Data
US 2021/0313021 A1    Oct. 7, 2021

(51) Int. Cl.
*G16H 10/60*    (2018.01)
*G16H 40/67*    (2018.01)

(52) U.S. Cl.
CPC ............. *G16H 10/60* (2018.01); *G16H 40/67* (2018.01)

(58) Field of Classification Search
None
See application file for complete search history.

(56) References Cited

U.S. PATENT DOCUMENTS

| | | | | |
|---|---|---|---|---|
| 2010/0138235 A1* | 6/2010 | Marks | .................... | G16H 40/67 705/2 |
| 2011/0264466 A1* | 10/2011 | Green, III | .............. | G16H 10/20 705/3 |
| 2012/0035954 A1* | 2/2012 | Yeskel | ................... | G06Q 10/10 705/3 |
| 2012/0215560 A1* | 8/2012 | Ofek | ....................... | G16H 10/00 705/3 |
| 2014/0073880 A1* | 3/2014 | Boucher | ................ | A61B 1/227 600/301 |
| 2018/0060538 A1* | 3/2018 | Tiwari | ................... | G16H 10/60 |
| 2019/0311810 A1* | 10/2019 | Sevenster | ............. | G16H 50/70 |
| 2021/0233658 A1* | 7/2021 | Van Assel | ............. | G16H 70/40 |

FOREIGN PATENT DOCUMENTS

KR           101440926 B1 *   9/2014
WO    WO-2020135951 A2 *   7/2020  ......... G06Q 10/1053

OTHER PUBLICATIONS

Vaccarino et al., "Brain-CODE: A Secure Neuroinformatics Platform for Management, Federation, Sharing and Analysis of Multi-Dimensional Neuroscience Data", May 23, 2018, Frontiers in Neuroscience Technology Report, May 2018, vol. 12, Article 28. (Year: 2018).*

* cited by examiner

*Primary Examiner* — Gregory Lultschik
*Assistant Examiner* — Anne-Marie K Alderson
(74) *Attorney, Agent, or Firm* — Snell & Wilmer L.L.P.

(57) ABSTRACT

The method includes receiving a request for relevant subject health information associated with a subject for a clinical trial; matching a subject identifier associated with the subject to a patient identifier; transmitting a health data query comprising the patient identifier to at least one of an electronic health record (EHR) system or a data transfer application programming interface to obtain EHR data associated with the subject; receiving the EHR data associated with the patient identifier; parsing the EHR data into relevant EHR data and nonrelevant EHR data; applying an EDC mapping function to the relevant EHR data; and/or producing EDC clinical data in a final standardized data set usable in an EDC system in response to the applying the EDC mapping function to the relevant EHR data.

17 Claims, 5 Drawing Sheets

Demographics 170

| | |
|---|---|
| Date of Birth | 28/MAR/2013 — 172<br>DD/MON/YYY(EN) |
| Gender | ○ Male ● Female — 174 |
| Race | Black — 176 |
| Nationality | African American — 178 |
| Ethnic Group | Non Spanish speaking, Non Hispanic — 182 |

FIG. 2

| Select | DATA | | | | | |
|--------|------|----------|--------|------|-----------|
| | Date | Lab Test | | Result | Unit | Range |
| ● | 2017-11-20 | Cholesterol in HDL | ↓↱312 | 54 | mg/dL | <40 |
| | 2017-11-20 | Free Fatty Acid | ↓↱314 | 1.28 | mmol/L | 0.26-6.00 |
| | 2017-11-20 | Triglycerides | ↓↱316 | 66 | mg/dL | <160 |
| | 2017-11-20 | Total Cholesterol | ↓↱318 | 90 | mg/dL | <200 |
| | Date | Lab Test | | Result | Unit | Range |
| ○ | 2017-11-21 | Cholesterol in HDL | ↓↱322 | 55 | mg/dL | <40 |
| | 2017-11-21 | Free Fatty Acid | ↓↱324 | 1.28 | mmol/L | 0.26-6.00 |
| | 2017-11-21 | Triglycerides | ↓↱326 | 68 | mg/dL | <160 |
| | 2017-11-21 | Total Cholesterol | ↓↱328 | 110 | mg/dL | <200 |

HEALTH INFORMATION EXCHANGE SYSTEM

FIELD

The present disclosure generally relates to health information collecting, processing, mapping, and exchange.

BACKGROUND

The recording of raw healthcare data of patients or subjects may vary widely between geographic areas, healthcare practitioners, healthcare organizations or institutions, data systems, entry of collected data into electronic systems, and/or the like. Accordingly, there may be little or no standardization between systems storing raw electronic healthcare data. Therefore, the transfer of raw electronic healthcare data from one system to a destination system may be difficult because the raw electronic healthcare data may not be in a form that is usable in the destination system.

These data structure issues become especially relevant when transferring raw electronic healthcare data to an electronic data collection (EDC) form for a clinical trial, for example, for communication with a regulatory body. While raw electronic healthcare data coming from healthcare practitioners, for example, may vary widely (e.g., with disparate options for information categories) and may be unstructured, an EDC form may comprise a set number of options for each information category and may be highly standardized and/or structured (e.g., in a table or chart form). Furthermore, the patient identifier in raw electronic healthcare data may be the patient's name or other personally-identifying information. For an EDC form, personally-identifying information may not be compliant with applicable laws or regulations, and therefore, the raw electronic healthcare data may be difficult to assign to a subject in a clinical trial applicable to an EDC form.

SUMMARY

A system, method, and article of manufacture (collectively, the "system") relating to health information exchange are disclosed herein. The system may be configured for receiving, processing, mapping, formatting, exchanging, presenting and/or otherwise utilizing health information. In various embodiments, the system may perform operations including receiving, by a processor, a request for relevant subject health information associated with a subject for a clinical trial; matching, by the processor, a subject identifier associated with the subject to a patient identifier; transmitting, by the processor, a health data query comprising the patient identifier to at least one of an electronic health record (EHR) system or a data transfer application programming interface to obtain EHR data associated with the subject; receiving, by a processor, the EHR data associated with the patient identifier; parsing, by the processor, the EHR data into relevant EHR data and nonrelevant EHR data; applying, by the processor, an EDC mapping function to the relevant EHR data; and/or producing, by the processor, EDC clinical data in a final standardized data set usable in an EDC system in response to the applying the EDC mapping function to the relevant EHR data. In various embodiments, the EHR data received is transformed raw data comprising a structured format.

In various embodiments, the health data query to the EHR system may comprise a data characteristic indicating the EHR data, and the received EHR data associated with the patient identifier may comprise the data characteristic. In various embodiments, parsing the EHR data may comprise reviewing the EHR data for a relevance indicator comprised in EHR data points of the EHR data, and separating the EHR data points comprising the relevance indicator from the EHR data points missing the relevance indicator. In various embodiments, the EDC mapping function may transform the relevant EHR data into the EDC clinical data. In various embodiments, applying the EDC mapping function to the relevant EHR data may comprise analyzing and transforming the relevant EHR data to the EDC clinical data. In various embodiments, applying the EDC mapping function to the relevant EHR data may further comprise removing the relevant EHR data not pertinent to the trial.

In various embodiments, the operations may further comprise applying, by the processor, a data mapping function to a data category in the received EHR data to associate the data category in the received EHR data with a corresponding data category in the final standardized data set before parsing the EHR data. In various embodiments, the operations may further comprise presenting, by the processor, the relevant EHR data on a user interface requesting confirmation by a user that the relevant EHR data is relevant before applying the EDC mapping function. In various embodiments, the operations may further comprise confirming, by the processor, at least one of relevance of the relevant EHR data or accuracy of the produced EDC clinical data. In various embodiments, the operations may further comprise presenting, by the processor, the EDC clinical data on a user interface requesting confirmation by a user that the produced EDC clinical data is accurate. In various embodiments, the operations may further comprise receiving, by the processor, a confirmation response indicating whether the EDC clinical data is accurate. In response to a confirmation response indicating that the EDC clinical data is not accurate, the operations may further comprise adjusting, by the processor, the EDC mapping function and reapplying the EDC mapping function to the relevant EHR data.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

FIG. 2 shows a display of patient information resulting from data points and associated metadata, in accordance with various embodiments;

FIG. 3 shows a user interface for presenting health data to a user of an exemplary health information exchange system, in accordance with various embodiments;

DETAILED DESCRIPTION

Figure 1:
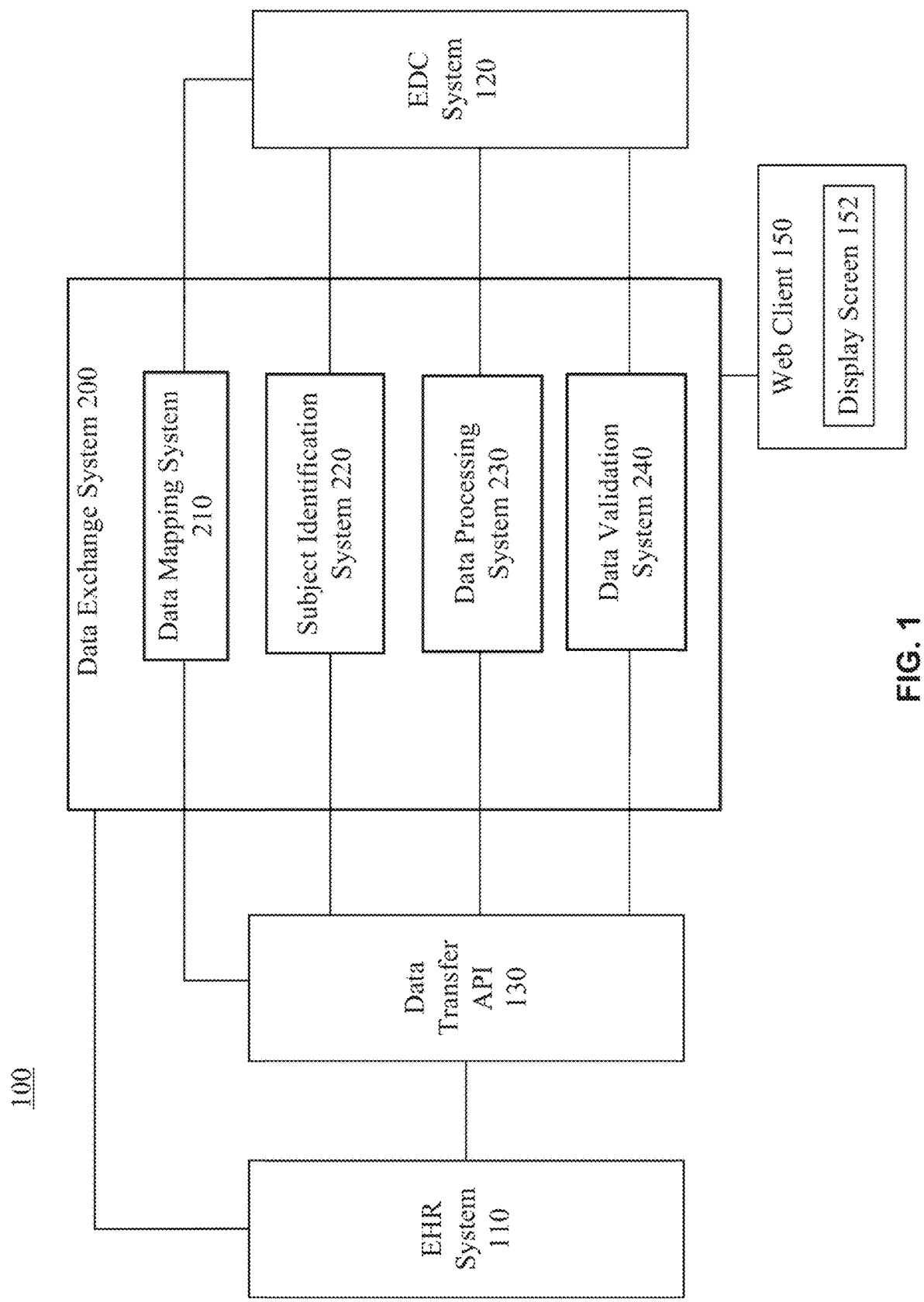
FIG. 1 shows an exemplary health information exchange system, in accordance with various embodiments.

With reference to FIG. 1, in accordance with various embodiments, an exemplary health information exchange system 100 is depicted. System 100 may comprise an electronic health record (EHR) system 110, an electronic data collection system (EDC) 120, a data transfer application programming interface (API) 130, a data exchange system 200, and/or a web client 150. In various embodiments, system 100 may comprise more than one of each component, e.g., more than one EHR system 110, EDC system 120, data transfer API 130, and/or data exchange system 200. In operation, system 100 (and/or its components) may be configured to receive data EHR data from EHR system 110, for example, through data transfer API 130, and perform various processing and data transformation and validation tasks on the EHR data received. System 100, and any of the components comprised therein, may be computer-based, and may comprise a processor, a tangible non-transitory computer-readable memory, and/or a network interface. Instructions stored on the tangible non-transitory memory may allow system 100 or any of its components to perform various functions, as described herein.

In various embodiments, EHR system 110 may comprise hardware and/or software components. For example, EHR system 110 may comprise a server appliance running a suitable server operating system (e.g., MICROSOFT INTERNET INFORMATION SERVICES or, "IIS") and having database software (e.g., ORACLE) installed thereon. EHR system 110 may be in electronic communication with EDC system 120, data transfer API 130, data exchange system 200, and/or web client 150. In various embodiments, EHR system 110 may be a system comprising and/or storing raw EHR data.

In various embodiments, the raw EHR data stored in EHR system 110 may be patient healthcare information entered into an electronic system, for example, at a physician's office, outpatient clinic, surgical center, hospital, or the like. As discussed, system 100 may comprise multiple EHR systems 110, each of which may record the EHR data for the respective patients in varying manners. For example, a first EHR system 110 may comprise X number of possible ethnicities for a patient to choose from, while a second EHR system 110 may comprise Y number of possible ethnicity values. As another example of the differences in raw EHR data between EHR systems 110, the abbreviations for various data points may differ between EHR systems 110. As yet another example of the differences in raw EHR data between EHR systems 110, the raw EHR data in EHR systems 110 may be recorded in an unstructured manner (e.g., without organization within a table or other pre-defined data model), or in different structures (e.g., on different documents or forms, tables, or spreadsheets having different rows, columns, categories, etc., each not necessarily sharing the same data model). The aggregate data received by data transfer API 130 and/or data exchange system 200 may be considered "big data."

In various embodiments, raw EHR data may be associated with a respective patient. The patient may be identified within EHR system 110 by name, social security number, and/or other a patient identifier. In various embodiments, the raw EHR data associated with a respective patient may comprise a tag or other marker that matches or is associated with the patient identifier for the respective patient. The patient identifier comprised in raw EHR data may comprise personally-identifying information, such as a patient name, birthdate, age, identifying number (e.g., a social security number), home address, phone number, any other information that personally identifies the patient, and/or combinations of the same. In that regard, combinations of personally-identifying information and/or data encoded with the same may act as a patient identifier. Accordingly, the user identifier may comprise a series of numbers, letters, and/or other symbols that uniquely identifies the patient.

In various embodiments, EDC system 120 may comprise hardware and/or software components. For example, EDC system 120 may comprise a server appliance running a suitable server operating system (e.g., MICROSOFT INTERNET INFORMATION SERVICES or, "IIS") and having database software (e.g., ORACLE) installed thereon. In various embodiments, EDC system 120 may be a system comprising and/or storing electronic data capture (EDC) data. EDC system 120 may be in electronic communication with EHR system 110, data transfer API 130, data exchange system 200, and/or web client 150.

In various embodiments, the EDC data captured and/or stored by EDC system 120 may be used for a clinical trial and analysis of the trial results as associated with the EDC data (e.g., for approval of a pharmaceutical drug by a regulatory body). Therefore, EDC data may be referred to as "EDC clinical data." For example, EDC clinical data may comprise life science (e.g., biological, chemical, biochemical, anatomical, biophysical, etc.) data. EDC clinical data may comprise at least a portion of data that corresponds to raw EHR data, and/or additional data not found in EHR data. The EDC clinical data corresponding to raw EHR data may be limited and/or more focused relative to raw EHR data described above. For example, EHR data may comprise 921 possible values to indicate patient's race, and a race indication for a patient may comprise multiple values to indicate multiple races. EDC system 120, on the other hand, may allow a limited value option for a subject's race, for example, selection of one race from six options for the subject. EDC clinical data may be more focused and/or structured relative to raw EHR data in EHR system 110, adhering to a rigid data model, in various embodiments. Moreover, the EDC system 120 may use a data model that is standard across regulatory bodies. In that regard, the EDC system 120 may employ a data model that is consistent or uniform for any part engaging in clinical research for submission before a regulatory agency that uses a given data model. Stated another way, the EDC system 120 may employ a data model that is useful across an industry. For example, EDC clinical data may comprise a standardized structure of a table or spreadsheet having columns and rows comprising the same EDC clinical data point type (e.g., race, height, weight, age, etc.) in each cell. As a further example, EDC system 120 may employ the Standard Data Tabulation Model (SD™), which the United States Food and Drug Administration utilizes. In various embodiments, EDC system 120 may employ the Clinical Data Interchange Standards Consortium (CDISC)'s Clinical Data Acquisition Standards Harmonization (CDASH) format. However, in various embodiments, EDC system 120 may employ and/or be able to export into the CDISC Study Data Tabulation Model (SDTM) format. Use of such a standardized and structured data models by EDC system 120 may streamline and/or facilitate data analysis, reporting, sharing, review, management, aggregation, warehousing, mining, and/or the like. Any EDC clinical data added to EDC system 120 may require formatting consistent with the EDC data model utilized in EDC system 120 in order to be usable in EDC system 120. For example, certain data points or entries within the standardized and structured data model may comprise standard terminology, terms, variables, abbreviations, and/or the like.

In various embodiments, data transfer API 130 may comprise hardware and/or software components. For example, data transfer API 130 may comprise a server appliance running a suitable server operating system (e.g., MICROSOFT INTERNET INFORMATION SERVICES or, "IIS") and having database software (e.g., ORACLE) installed thereon. In various embodiments, data transfer API 130 may be a system configured to restructure raw data (e.g., raw EHR data) into a standardized form readable and/or usable by another system(s). Data transfer API 130 may be in electronic communication with EHR system 110, EDC system 120, data exchange system 200, and/or web client 150.

In various embodiments, data transfer API 130 may receive a query for health data, for example, from data exchange system 200 and/or EDC system 120. A health data query may comprise a request for EHR data about a certain subject, and/or comprising a certain data characteristic, indicating the EHR data desired. A subject may comprise, and/or a data characteristic (e.g., a data parameter) may indicate, a patient, a group of patients, a patient belonging to a certain demographic (e.g., people having certain characteristics, such as gender, race, age (range), disease, height, weight, and/or the like), a disease, treatment, diagnosis, and/or the like which may be of interest. Data transfer API 130 may be configured to retrieve raw EHR data relevant to the health data query received from data exchange system 200 and/or EDC system 120. To do so, data transfer API 130 may create a data query having the data characteristic indicating the EHR data desired, and then obtain raw EHR data having the data characteristic. For example, the data query may indicate that the desired EHR data is related to a specific patient for a certain time period. Data transfer API 130 may review raw EHR data and/or obtain raw EHR data for the patient during the time period (e.g., EHR data having the data characteristic). The data characteristic may be a tag or meta data comprised in or associated with the raw EHR data, thus allowing data transfer API 130 to identify that EHR data relevant to the data query (e.g., the relevant data comprises the tag or meta data indicating that the data comprises the desired data characteristic). For example, a data characteristic of EHR data may be matched with a code in the Logical Observation Identifiers Names and Codes (LOINC) database and/or Systematized Nomenclature of Medicine (SNOMED) code database to identify the EHR data (e.g., identify the medical data point(s) and their meaning, category, applicability, etc.).

In response to obtaining the raw EHR data from EHR system 110, data transfer API 130 may create a structured data set. To do so, data transfer API 130 may identify data points, and/or data characteristics of data points, that are associated with data categories or data fields recognized by data transfer API 130. For example, for data points associated with a patient's personally-identifying information, data transfer API 130 may review the raw EHR data for data resembling a name, birthdate, address, and/or the like. In response to identifying data points of raw EHR data associated with a data category recognized by data transfer API 130, data transfer API 130 may tag such data point with a marker (or other type of meta data) indicating the associated data category, and/or data transfer API 130 may transform such identified data points into a format or language associated with data transfer API 130 (e.g., a structured format). In various embodiments, data transfer API 130 may anonymize EHR data and/or data comprised in the structured data set, for example, by assigning a patient identifier to the patient that is not indicative of any of the patient's personally-identifying information. Thus, the patient's privacy may be better maintained, for example, to comply with governmental regulation.

In various embodiments, the structured data set may comprise the health information comprised in the obtained raw EHR data, but in a format that is compatible and/or usable by other systems. For example, in various embodiments, data transfer API 130 may transform the raw EHR data into a structured format, wherein each data point may have an assigned position in the structured format, such as a cell within a table of rows and columns. In various embodiments, the structured format may comprise meta data that indicates or describes different aspects of data points within the structured data set. Continuing with the example above involving health information about a specific patent for a certain time period, the structured data set created by data transfer API 130 based on the raw EHR data obtained from EHR system 110 may comprise information about the patient such as static (or substantially static) information, such as name, birthdate, eye color, gender, and/or the like, or dynamic information such as height, weight, body temperature, blood pressure, cholesterol level, heart rate, treatments, medications, prescriptions, diagnoses, and/or other information measured or collected at various times (e.g., during doctor's office or hospital visits by the patient, during clinical trials, or the like). The structured data set may be input and/or transformed into the structured format associated with data transfer API 130. In various embodiments, the structured data set may comprise meta data describing the structure and/or components of the structured data set. For example, such meta data may describe what a certain data point is and/or to what a data point or set of data points relates, such as would occur using an XML or JSON data structure. In various embodiments, for example those using a delimited structure, the meta data indicates where in the structured data set to find certain data points, data sets, or data categories (e.g., a first position or property of the structured data set may comprise a patient name, a second position or property of the structured data set may comprise a patient birthdate/age, etc.).

Those data sets using a tree data structure (e.g., an XML or JSON data structure), with reference to FIG. 2 and Table 1, below, the meta data or tags may indicate what the data point or set of data points is and/or to what such data point(s) relates. For example, Table 1 shows the demographic information (which may be the root element in this example) for a patient or subject, or group of patients or subjects.

TABLE 1

| Demographics [DM] Item Name/SAS Variable | Front End Form Question Text |
|---|---|
| BRTHDAT[BRTHDAT] | Date of Birth |
| SEX[SEX] | Gender |
| RACE[RACE] | Race |
| NATION[NATION] | Nationality |
| ETHNIC[ETHNIC] | Ethnic Group |

Accordingly, the characteristics listed in Table 1 and shown in FIG. 2 may be under the tag "DM" for demographics. Information in the tree data structure under demographic information having a tag "BRTHDAT" may be the patient's birthdate (which would be displayed in the second column of Table 1, and shown on a demographics graphical user interface (GUI) 170, shown in FIG. 2, as birthdate 172). Information in the tree data structure under demographic information having a tag "SEX" may be the patient's sex or gender (which would be displayed in the second column of Table 1, and shown on demographics GUI 170 as gender 174). Information in the tree data structure under demographic information having a tag "RACE" may be the patient's race (which would be displayed in the second column of Table 1, and shown on demographics GUI 170 as race 176). Information in the tree data structure under demographic information having a tag "NATION" may be the patient's nationality (which would be displayed in the second column of Table 1, and shown on demographics GUI 170 as nationality 178). Information in the tree data structure under demographic information having a tag "ETHNIC" may be the patient's ethnicity (which would be displayed in the second column of Table 1, and shown on demographics GUI 170 as ethnicity 182). The metadata or tags to indicate to what the information associated therewith relates may be any suitable metadata or tag.

As discussed, in various embodiments, the structured format of the structured data set may comprise a table wherein each cell, row, or column comprises a certain data point (e.g., each row may be associated with a discrete patient, and column one may be comprise the patient name, column two may comprise the patient birthdate, etc.). In various embodiments, the structured format may comprise standardized health data points comprising meta data comprised therein and/or associated therewith. For example, a standardized health data point may comprise meta data (e.g., a data marker, indicator, and/or the like) indicating what information (or a data characteristic thereof) is in a certain portion of the structured data set (e.g., personally-identifying information, weight information, height information, age information, vital signs information, diagnoses, treatments, and/or the like).

An example of data transfer API 130 may be the Fast Healthcare Interoperability Resources (FHIR®) API or system. In such an example, the structured data set and structured format would be data in FHIR resource format.

In various embodiments, data exchange system 200 may comprise hardware and/or software components. For example, data exchange system 200 may comprise a server appliance running a suitable server operating system (e.g., MICROSOFT INTERNET INFORMATION SERVICES or, "IIS") and having database software (e.g., ORACLE) installed thereon. In various embodiments, data exchange system 200 may be a system or application configured to transmit a query to data transfer API 130 and/or EHR system 110 to obtain health data associated with a certain subject, topic, study, and/or the like. Data exchange system 200 may be configured to receive such health data, and review and transform the health data into standardized health data relevant, compatible, and/or usable by another system (e.g., EDC system 120). Data exchange system 200 may be in electronic communication with EHR system 110, EDC system 120, data transfer API 130, and/or web client 150.

In various embodiments, data exchange system 200 may comprise various components configured to perform the functions of data exchange system 200, such as data mapping system 210, subject identification system 220, data processing system 230, and/or data validation system 240. However, the components of data exchange system 200 are discussed for illustrative and exemplary purposes only. Therefore, data exchange system 200 may comprise any components therein configured to perform the functions discussed in relation to those performed by data exchange system 200 and its components.

In various embodiments, in response to the health data query being sent to data transfer API 130, and data transfer API 130 obtaining and producing the structured data set comprising the relevant health data, data exchange system 200 may perform various processes on the structured data set. In various embodiments, data mapping system 210 may be configured to identify which data categories or fields in the structured data set correspond to the data categories or fields comprised in a final standardized data set (e.g., which data categories, or data tags or indicators associated therewith, relating to a patient's name in the structured data set correspond to the data categories, or data tags or indicators associated therewith, relating to a patient's name in the final standardized data set). For example, the final standardized data set may comprise a structured data format compatible with EDC system 120 (e.g., a data format that EDC system 120 can accept, read, store, and/or use).

In various embodiments, to identify the data categories in the structured data set corresponding to the data categories in the final standardized data set, data mapping system 210 may comprise a meta data mapping function. The meta data mapping function may comprise a function which, in response to being applied to a data category in the structured data set, may indicate the data category in the final standardized data set associated therewith. In various embodiments, the meta data mapping function may provide a key or legend indicating which data categories in the structured data set are associated with which data categories in the final standardized data set. For example, data mapping system 210 may identify that a first data indicator or meta data tag for a first data category in the structured data set may correspond to a second data indicator or meta data tag for a second data category in the final standardized data set. In response, data mapping system 210 may associate the first data category in the structured data set and the data points therein with the second data category in the final standardized data set.

In various embodiments, data mapping system 210 may indicate which data location in the structured data set (e.g., a row, column, and/or cell in a table of data points in the structured data set) may relate or corresponds to which data location in a final standardized data set. For example, data mapping system 210 indicate that a first row of data in the structured data set comprises a patient's birthdate, which corresponds to the second row in the final standardized data set. In various embodiments, data mapping system 210 may mark the data locations and/or data categories in the structured data set (e.g., with a data marker, tag, or meta data) to indicate to which data locations and/or data categories in the final standardized data set the same correspond.

In various embodiments, subject identification system 220 may be configured to identify which patient (to whom the health data in the structured data set and associated raw EHR data belongs) corresponds to and/or is associated with which subject (and subject identifier) in the final standardized data set. As discussed, a patient identifier may be associated with the patient. The health data associated with the patient may comprise and/or be associated with the patient identifier to indicate that such health data is regarding that specific patient. As discussed, data transfer API 130 may provide the patient identifier to anonymize the EHR data and structured data set. The patient identifier may be the same for a particular patient across multiple events in the EHR data (e.g., doctor or hospital visits, tests, lab results, and/or the like). In various embodiments, subject identification system 220 may further be configured to identify any studies, clinical trials, or the like in which the patient is enrolled or participating.

In various embodiments, EDC system 120 and/or data exchange system 200 may assign a subject identifier associated with the subject of a clinical trial. The subject may correspond to the patient, disease, medical topic, treatment, and/or the like, associated with and/or comprised in the obtained EHR data and/or the structured data set. The subject identifier may be purposed to anonymize the subject (if the subject is a person) similar to the patient identifier. An individual (i.e., a patient or subject) may be participating in multiple tests, trials, and/or the like. In various embodiments, for each test or trial, the individual may have a different subject identifier associated therewith (i.e., each subject identifier is specific to a certain trial or test, regardless if the same individual is associated with multiple trials or tests). If a subject is not enrolled in EDC system 120 and/or data exchange system 200, user of EDC system 120 and/or data exchange system 200 may enroll the subject by entering the subject's information therein. For a subject who is an individual, enrolling the subject in EDC system 120 and/or data exchange system 200 may comprise entering and/or selecting the subject's personally-identifying information, the disease, treatment, diagnosis, a study, and/or any other required information for the related study (e.g., a clinical trial) in EDC system 120 and/or data exchange system 200. In response, EDC system 120 and/or data exchange system 200 may create and/or assign a subject identifier to the subject, associating the subject identifier with at least a portion of the entered required information.

The health data query (which may be created in EDC system 120 and/or data exchange system 200 based on a query request indicating the subject and data categories and characteristics of interest) may comprise the subject's personally-identifying information and/or the subject's subject identifier. In various embodiments, after a subject has been entered into EDC system 120 and/or data exchange system 200, only the subject identifier is used to indicate the subject, thus at least partially anonymizing health data associated therewith. Subject identification system 220 may associate the subject's patient identifier (e.g., provided by data transfer API 130) with the subject identifier. The subject identifier and the patient identifier associated with the same person, study, organization, and/or the like may therefore be mapped together as being associated. Therefore, subject identification system 220 may comprise an identifier mapping function, which may be applied to a subject identifier (and/or a patient identifier) to identify an associated patient identifier (and/or subject identifier), or vice versa. In various embodiments, because a single patient identifier may be associated with a patient for multiple tests/trials, and a separate subject identifier may be issued for each test/trial in which a subject (e.g., the same individual as the patient) participates, the identifier mapping function may be configured to identify multiple subject identifiers being associated with a single patient identifier, or vice versa. The mapping between a patient identifier (e.g., used in data transfer API 130 and/or EHR system 110) and a subject identifier (e.g., used in EDC system 120) may be encrypted such that a patient or subject's identity cannot readily be discerned. The patient identifier may allow data transfer API 130 to obtain the raw EHR data associated with the patient (and therefore the subject). The health data obtained associated with the patient identifier and/or subject identifier may allow health data procurement without specifically or personally identifying the patient and/or subject.

In various embodiments, data processing system 230 may be configured to identify relevant health data (e.g., from the structured data set from data transfer API 130 that will be relevant to EDC system 120). Data processing system 230 may review the structured data set from data transfer API 130 to identify relevant health data and not relevant health data. To do so, data processing system 230 may review the structured data set for data characteristics of data points comprised in the structured data set. Data processing system 230 may comprise and/or recognize meta data (e.g., data markers, tags, and/or identifiers) that are associated with relevant health data of interest to data exchange system 200. Accordingly, data processing system 230 may review the structured data set and identify the data points comprised therein having and/or being associated with the meta data recognized by data processing system 230, and may identify data points comprised in the structured data set lacking such meta data. The data points having and/or being associated with the meta data recognized by data processing system 230 may be identified and/or otherwise marked (e.g., with a relevance data marker) as relevant health data to data exchange system 200 and/or EDC system 120. The data points lacking the meta data recognized by data processing system 230 may be separated from the other data points in the structured data set or otherwise discarded.

As an illustrative example, the query to data transfer API 130 from data exchange system 200 may be seeking health data for a specific patient regarding a certain disease. Therefore, data processing system 230 may be searching for data points from the structured data set comprising certain meta data indicating that such data points are relevant to the query (e.g., data points having certain data characteristics associated with the meta data, such as meta data indicating that the data is specifically regarding the disease or patient, from a certain physician or hospital wherein check-ins associated with the disease were taken, at a certain time of day when such a check-in would take place, and/or any other data characteristics that would distinguish a data point as relevant). Following this example, data processing system 230 may identify a data point(s) lacking the desired metadata or tag. For example, the patient may have visited an emergency room for a condition unrelated to the disease relevant to the health data query (e.g., a broken bone occurring at night). Data processing system 230 may recognize that the data points associated with this event do not comprise the meta data associated with the desired heath data. For example, data processing system 230 may identify a lack of the desired meta data tags, therefore, identifying such data points as not relevant. As another example, data processing system 230 may identify meta data tags associated with the data points that indicate that such data points are not relevant (e.g., a tag on the data points indicating that the medical event was at night and at an emergency room, and none of the medical check-ins for the disease of interest were at night or in an emergency care setting). In response to identifying the relevant health data, the not relevant health data may be set aside or otherwise discarded. That is, the not relevant health data may be excluded from the data conversion of the structured data set received from data transfer API 130 to the final standardized data to be transferred to EDC system 120.

In various embodiments, data processing system 230 may be configured to confirm whether health data in the structured data set is relevant with a user of data exchange system 200. In various embodiments, data processing system 230 may comprise instructions regarding data points having certain characteristics (e.g., certain metadata and/or tags associated therewith). Certain data characteristics may be predetermined to be discarded, passed through, or brought to the user's attention (e.g., to confirm whether the data is relevant to the inquiry). For example, data processing system 230 may present the health data from the structured data set to the user with a suggested relevance determination and asking for confirmation, and/or data processing system 230 may present the health data from the structured data set to the user requesting the user to choose whether the health data is relevant.

In various embodiments, data processing system 230 may be configured to transform or convert the health data in the structured data set to final standardized health data in a final standardized data set. As discussed herein, the final standardized data set may comprise a structured data format compatible with EDC system 120. Similar to EDC clinical data in the final standardized data set being limited or more focused relative to raw EHR data, as discussed herein, the EDC clinical data in the final standardized data set may also be limited relative to the health data in the structured data set. For example, there may be hundreds of value to indicate a patient's race in the health data of the structured data set, and multiple values may be allowed, but in the EDC clinical data in the final standardized data set, there may only be six options, of which only one can be selected. Therefore, data processing system 230 may comprise an EDC mapping function to apply to health data of the structured data set to transform the data into EDC clinical data in the final standardized data set. In various embodiments, data processing system 230 may comprise a conversion feature in which a user of data exchange system 200 may supply an EDC mapping function to apply to health data of the structured data set to transform the data into EDC clinical data in the final standardized data set. In this manner, the user may tailor the EDC mapping function to be specifically design for a certain study (e.g., clinical trial).

The EDC mapping function may comprise rules for analyzing the health data from the structured data set to transform the same into EDC clinical data. For example, one rule may indicate that there is no mapping between a data point value in the health data from the structured data set to the EDC clinical data (i.e., the data point value in the health data from the structured data is simply transferred to the EDC clinical data). As another example, one rule may indicate that a data point value in the health data from the structured data set is directly equal to a corresponding data point value in the EDC clinical data. Going along with the options to indicate race within health information, the EDC mapping function for a subject's race may indicate that a value of Caucasian or any European race (e.g., French, Italian, German, Scandinavian) is equal to a value of "white" in the EDC clinical data. Another example of an EDC mapping function rule may indicate that if multiple data points are selected for a data category, the first value, or a certain value, should be presumed to be the dominant characteristic. Going along further with the options to indicate race within health information, the EDC mapping function for a subject's race may indicate that a value of African with at least one other race value will transform into a race category value of "African" in the EDC clinical data. Along similar lines, the EDC mapping function may assign and/or associate weights with certain health data value within data categories in the structured data set which may determine the data point value for a data category in the final standardized data set. For example, the presence of a first value with a higher weight than a second value in the structured data set may cause data processing system 230 to transform the data in that data category to a data value in the EDC clinical data that is equal, or more similar, to the first value. The mapping function may also indicate which data points in which locations of the structured data set may correspond to the data point locations in the final standardized data set.

Accordingly, because the final standardized data set is limited or more focused relative to the other health data types, data processing system 230 may apply the mapping function to the health data in the structured data set to transform the same into EDC clinical data in a final standardized data set.

In various embodiments, data validation system 240 may be further configured to for the accuracy of the transformation of the health data in the structured data set into EDC clinical data in the final standardized data set. As discussed herein, data having certain characteristics may cause data processing system 230, data validation system 240, and/or data validation system 240 to seek confirmation of the accuracy of the produced EDC clinical data. For example, a patient's race data in the structured data set, because of the hundreds of possible values, may trigger presentation of data to a user or other decision-making module to determine the appropriate format (e.g., the appropriate value from the possible six values for race in EDC clinical data) for migration to EDC system 120. For example, data processing system 230 may present (e.g., on web client 150) the EDC clinical data value resulting from applying the EDC mapping function to the associated health data value(s) from the structured data set asking for confirmation of the same, and/or data processing system 230 may present the possible EDC clinical data values and the associated health data value(s) from the structured data to the user requesting the user to choose the correct EDC clinical data value(s) based on the associated health data value(s) from the structured data. In this regard, systems in accordance with the present disclosure may create more efficient data transforms. By seeking confirmation regarding the relevance and accuracy of data, for example, data migration to EDC system 120 may experience an improvement in speed and accuracy.

In various embodiments, web client 150 may incorporate hardware and/or software components. For example, web client 150 may comprise a server appliance running a suitable server operating system (e.g., MICROSOFT INTERNET INFORMATION SERVICES or, "IIS"). Web client 150 may be any device that allows a user to communicate with a network (e.g., a personal computer, personal digital assistant (e.g., IPHONE®, BLACKBERRY®), tablet, cellular phone, kiosk, and/or the like). Web client 150 may be in electronic communication with EHR system 110, EDC system 120, data transfer API 130, and/or data exchange system 200. Web client 150 may allow the user of system 100 to interact with the other components of system 100. In various embodiments, web client 150 may comprise an input device (i.e., a physical or digital button), by which the user may select actions for web client 150 or system 100 (and the components therein) to take. For example, web client 150 may comprise display screen 152, which may display a graphical user interface (GUI) provided by data exchange system 200. Display screen 122 displaying portal 154 may allow the user to select an input device(s), which may be provided by the GUI or portal 154, to communicate to system 100 a desired action by system 100.

Web client 150 includes any device (e.g., personal computer, mobile device, etc.) which communicates via any network, for example such as those discussed herein. In various embodiments, web client 150 may comprise and/or run a browser, such as MICROSOFT® INTERNET EXPLORER®, MOZILLA® FIREFOX®, GOOGLE® CHROME®, APPLE® Safari, or any other of the myriad software packages available for browsing the internet. For example, the browser may communicate with a server via network by using Internet browsing software installed in the browser. The browser may comprise Internet browsing software installed within a computing unit or a system to conduct online transactions and/or communications. These computing units or systems may take the form of a computer or set of computers, although other types of computing units or systems may be used, including laptops, notebooks, tablets, handheld computers, personal digital assistants, set-top boxes, workstations, computer-servers, mainframe computers, mini-computers, PC servers, pervasive computers, network sets of computers, personal computers, such as IPADS®, IMACS®, and MACBOOKS®, kiosks, terminals, point of sale (POS) devices and/or terminals, televisions, or any other device capable of receiving data over a network. In various embodiments, browser may be configured to display an electronic channel.

Referring now to FIGS. 2 and 3, the process flows depicted merely reflects embodiments and is not intended to limit the scope of the disclosure. For example, the steps recited in any of the method or process descriptions may be executed in any order and are not limited to the order presented. It will be appreciated that the following description makes appropriate references not only to the steps and user interface elements depicted in FIGS. 2 and 3, but also to the various system components as described above with reference to FIG. 1.

Figure 4:
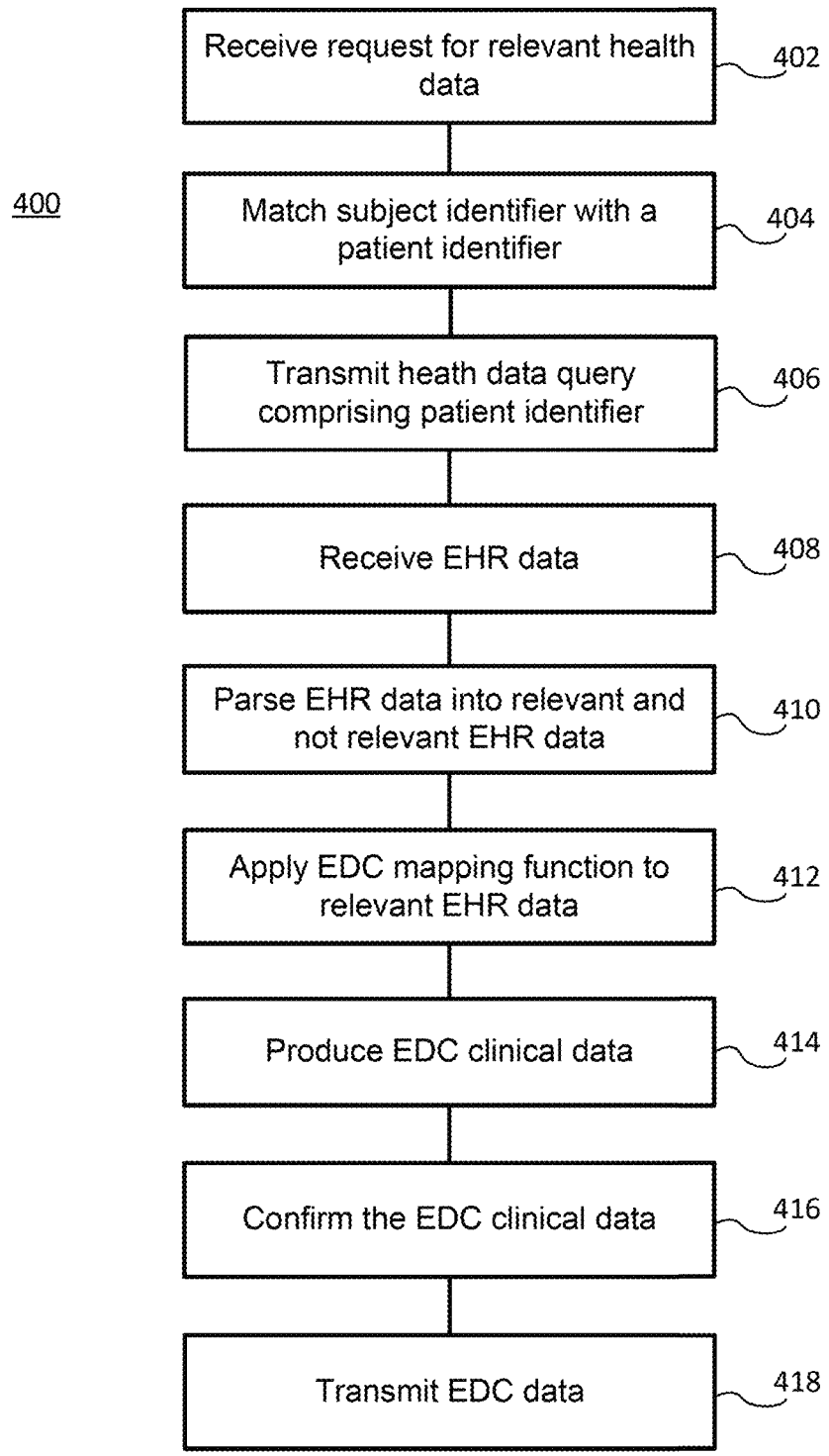
FIG. 4 shows a flowchart depicting an exemplary method for producing EDC clinical data, in accordance with various embodiments.

FIG. 4 depicts a method 400 for producing EDC clinical data (i.e., a final standardized data set), in accordance with various embodiments. Data exchange system 200 may receive a request for relevant health and/or clinical data (step 402). The request may be entered into data exchange system 200, and may indicate health and/or clinical data of interest (e.g., relating to a certain patient, study, trial, disease, treatment, etc.). The request may comprise a desired data characteristic(s), indicating one or more characteristics of relevant heath and/or clinical data. For example, relevant health and/or clinical data may comprise data characteristics indicating the specific patient, study, trial, disease, treatment, etc.

In various embodiments, the request may comprise an identifier for an individual associated with the requested health data. The identifier may be personally-identifying information or other information associated with the individual, a patient identifier, and/or a subject identifier. Data exchange system 200 and/or subject identification system 220 may match a subject identifier (e.g., an identifier relevant to EDC system 120) with a patient identifier (e.g., an identifier relevant to data transfer API 130) (step 404). The subject identifier and the patient identifier may be associated with the individual. The patient identifier and/or subject identifier may anonymize the health data associated therewith, for example, to comply with government regulations (e.g., such that the individual may not be personally identified). As discussed herein, the mapping between a patient identifier (e.g., used in data transfer API 130 and/or EHR system 110) and a subject identifier (e.g., used in EDC system 120) performed by data exchange system 200 may be encrypted such that a patient or subject's identity cannot readily be discerned.

In various embodiments, data exchange system 200 may create a health data query comprising the patient identifier and/or a data characteristic(s) indicating relevant health data. The health data query may be transmitted (step 406), for example, to data transfer API 130 and/or EHR system 110. In various embodiments, the health data query may be transmitted from data exchange system 200 to data transfer API 130. In response, data transfer API 130 may obtain raw EHR data from EHR system 110 and standardize the raw EHR data into a structured data set, as described herein. The data obtained by data transfer API 130 may comprise tags or markers indicating that the data is relevant to the health data query. That is, the data obtained may comprised the desired data characteristics indicated in the health data query (e.g., the health data is about the specific individual, study, disease, etc.). Data exchange system 200 may receive the structured data set comprising the EHR data (step 408).

In various embodiments, the health data query may be a periodic health data query, which data exchange system 200 may automatically transmit to data transfer API 130 after a certain time period has passed. For example, for dynamic health information such as height, weight, body temperature, blood pressure, cholesterol level, heart rate, treatments, medications, prescriptions, diagnoses, and/or other information that may change over time, data exchange system 200 transmit health data queries periodically to gather to most recent health data. For static health information, data exchange system 200 may only transmit one health data query, as such information may not change over time.

In various embodiments, the EHR data from data transfer API 130 may comprise discrete data points comprising health information having relatively small time differences between them. For example, EHR data points may have time stamps (or the like) indicating that such EHR data points are within between one and 12 hours from one another (e.g., within one hour, 2 hours, 4 hours, six hours, 12 hours, etc. from one another). In various embodiments, data exchange system 200 and/or data processing system 230 may be configured to group such data points into a data group or data set. A data group may comprise EHR data points that are related to, for example, one physician or hospital visit. For example, with additional reference to FIG. 3, data points 312-318 may comprise time stamps within two hours (or any other suitable duration) of each other, and therefore, may be grouped into first data set 310. Similarly, data points 322-328 may comprise time stamps within two hours (or any other suitable duration) of each other, and therefore, may be grouped into second data set 320.

In various embodiments, data exchange system 200 and/or data processing system 230 may review the EHR data in the structured data set for relevance. That is, data exchange system 200 and/or data processing system 230 may review the EHR data in the structured data set and identify desired data characteristics comprised in and/or associated with various data points, identify a lack of the desired data characteristics in various data points, and/or identify undesired data characteristics in various data points. In response to such a relevance review of the EHR data in the structured data set, data exchange system 200 and/or data processing system 230 may parse the EHR data into relevant and not relevant EHR data (step 410). EHR data comprising the desired data characteristics may be determined to be relevant, and EHR data lacking the desired data characteristics and/or comprising an undesired data characteristic may be determined to be not relevant. Not relevant data may be separated from relevant data and/or discarded. For example, if the respiratory rate along with blood pressure is collected for a subject during a hospital visit, but the relevant trial or study is only interested in respiratory rate, then the blood pressure data may be excluded from any informational presentation to a user and/or separated from the respiratory rate. In such an example, the meta data mapping function for data exchange system 200 and/or data processing system 230 may indicate that respiratory rate data is relevant and blood pressure data is not relevant. As another example, with reference to FIG. 3, if a triglycerides measurement (e.g., data points 316 and/or 326) is not relevant to the subject trial or study, data exchange system 200 and/or data processing system 230 may indicate or determine that such measurement or data point is not relevant and/or separate, or otherwise discard, the triglycerides measurements from data sets 310 and/or 320. In a related example, if only one data set between data sets 310 and 320 comprises a value for free fatty acid (e.g., data point 314 is 1.28 mmol/L, while data point 324 has no value), data exchange system 200 and/or data processing system 230 may determine that the entire data set 320 is not relevant because the specific trial or study of interest requires free fatty acid readings. Accordingly, data exchange system 200 and/or data processing system 230 may (automatically) discard or exclude data set 320, or otherwise separate data set 320, from data to be included in the final standardized data set utilized by EDC system 120.

In various embodiments, data exchange system 200 and/or data validation system 240 may evaluate the accuracy of the relevance determination (i.e., confirming the health data (step 416) to be relevant). For example, if the relevance of EHR data cannot be determined with a certain degree of certainty by data exchange system 200 and/or data processing system 230, and/or if a data point type of the EHR data (e.g., a data point have a certain characteristic) is predetermined as requiring confirmation, a confirmation may be presented to the user or other decision-making module of data exchange system 200 asking for an indication of whether the relevant determination is correct, and/or to determine if the presented EHR data is relevant. In various embodiments, a user may indicate if at least a portion of the group of data is relevant or not relevant.

For example, with reference again to FIG. 3, information associated with one or more hospital visits for a patient or subject, which data exchange system 200 and/or data processing system 230 cannot determine if such hospital visit is relevant with sufficient certainty, and/or such hospital visit information being predetermined as requiring confirmation, may be presented to a user for relevance confirmation. For example, a first hospital visit on 2017 Nov. 20 for a patient may have occurred, having a first data set 310 associated therewith, and a second hospital visit on 2017 Nov. 21 for the patient may have occurred, having a second data set 320 associated therewith. The first data set 310 may comprise health information, for example, reflected in data points 312-318, and the second data set 320 may comprise health information, for example, reflected in data points 322-328. The health information associated with the hospital visits may be presented on user interface 300 to determine whether one or both of first data set 310 and second data set 320 is relevant. The user or other decision-making module may indicate whether at least a portion of the presented information associated with one or more hospital visits is relevant. For example, the user or other decision-making module may indicate that a data point or data set is relevant by selecting the data point or data set, and/or selecting an input device associated with the relevant data point or data set. For example, as shown on user interface 300, first input device 302 (e.g., an electronic button) may be associated with first data set 310 and second input device 304 (e.g., an electronic button) may be associated with second data set 320. A user may select first input device 302 to indicate that first data set 310 is relevant and/or select second input device 304 to indicate that second data set 320 is relevant. In various embodiments, the user may be required indicate whether the entire group of information (e.g., all data points 312-318 associated with first data set 310 and/or all data points 322-328 associated with second data set 320) for an event (e.g., a hospital visit) is relevant or not relevant.

In response to determining the relevant EHR data of the structured data set from data transfer API 130, data exchange system 200 and/or data processing system 230 may apply an EDC mapping function to the relevant EHR data of the structured data set (step 412). The EDC mapping function, as discussed here, may be configured to produce EDC clinical data in a final standardized data set, which may be compatible with, and/or in a data model or structure utilized by EDC system 120.

EDC clinical data may be produced (step 414) in response to applying the EDC mapping function to the relevant EHR data of the structured data set. In response, the EDC clinical data may be confirmed (step 416). To do so, data exchange system 200 and/or data validation system 240 may analyze the produced EDC clinical data determine if one or more data points in the produced EDC clinical data are those predetermined to be brought to the user's attention (e.g., for confirmation). If a data point in the produced EDC clinical data is one of such datapoints, data exchange system 200 and/or data validation system 240 may present a confirmation request to the user (e.g., on display screen 152 of web client 150) or other decision-making module requesting confirmation that the EDC clinical data produced is correct, or requesting indication of which EDC clinical data should be produced based on the EHR data of the structured data set is accurate. For example, the user may enter which EDC clinical data should be produced in view of the associated EHR data, or the user may select the correct EDC clinical data from options presented by data exchange system 200 and/or data validation system 240.

In response to confirming the EDC clinical data produced, the EDC clinical data may be transmitted (step 418) to EDC system 120. The EDC clinical data may be stored in the final standardized format in the EDC system 120.

The methods and systems described herein improve the functioning of a computer, network, platform, data processing and/or operating environment (e.g., including a network(s), database(s), node(s), etc.), and/or the like. Such an environment may include one or more parties in (electronic) communication with one another, thus improving the efficiency of their interactions. For example, clinical trials (e.g., for regulatory agencies) may utilize EDC system 120. The clinical trial may, for example, be for the evaluation and possible approval of a pharmaceutical drug to treat a disease. Therefore, obtaining all the available raw EHR data from EHR system 110, and transforming such data into EDC clinical data in the final standardized format, may allow better planning of the clinical trial according to already-available health information. Such data gathering and transformation into a usable form may be extremely useful and beneficial, saving significant time which otherwise may have been wasted gathering, analyzing, and/or utilizing data that is already available. For example, the EHR data already existing may indicate that individuals who have the disease, which the pharmaceutical is designed to treat, have certain symptoms at certain stages of the disease, or are susceptible to certain things at various times. The clinical trial may be planned or scheduled accordingly. Additionally, with continual and/or periodic health data queries sent to EHR system 110, additional health data may be incorporated into the trial as it is obtained and transformed into EDC clinical data. Therefore, if trends are noticed in the subjects, symptoms, and/or the like, the clinical trial may adjust its course to adapt to such changes. Monitoring subjects only by visits to a specific locations associated with EDC system 120, which would collect data in the final standardized data format and use only such data, may not provide adequate information to adapt a clinical trial or study. Therefore, the ability to gather raw EHR data (e.g., from many sources) and transform such data into a usable form (the EDC clinical data in the final standardized data set) may be beneficial.

Figure 5:
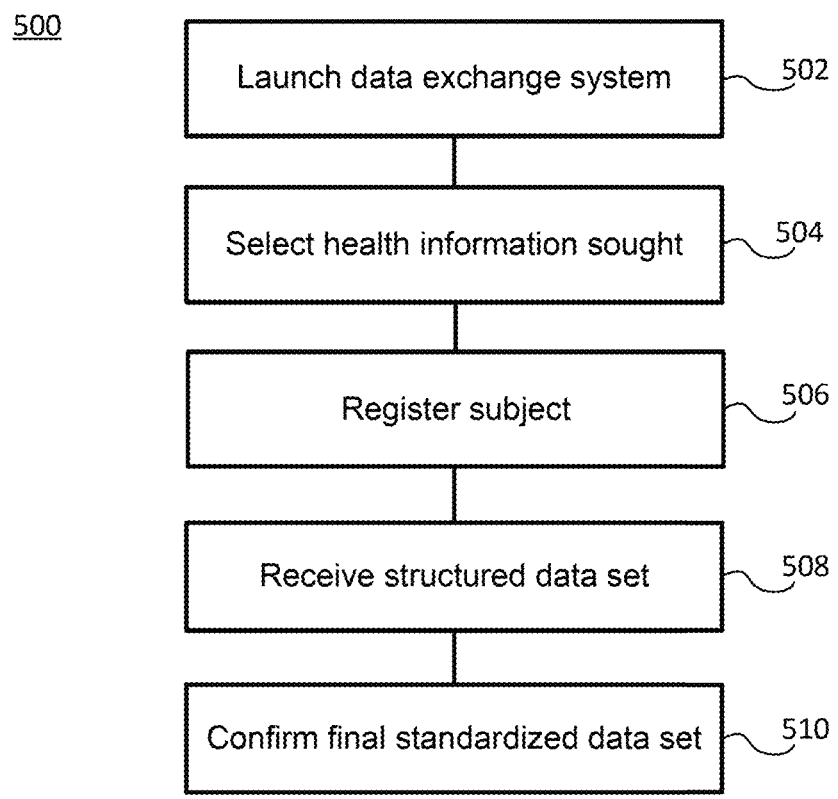
FIG. 5 shows a flowchart depicting an exemplary method for utilizing a data exchange system, in accordance with various embodiments.

FIG. 5 depicts a method 500 for utilizing data exchange system 200, in accordance with various embodiments. In various embodiments, data exchange system 200 may be an application on a web client 150. Therefore, a user may launch data exchange system 200 (step 502). In various embodiments, a user may register with data exchange system 200 by providing login information and/or required credentials (e.g., username, password, email address, etc.). Data exchange system 200 may be launched as a standalone application, and/or as part of or from EHR system 110 and/or EDC system 120.

To request health information (e.g., by creating a health data query), the user may select the health information sought (step 504), for example health information regarding a certain patient or subject, clinical trial, study, and/or any other desired information. To do so, in various embodiments, the user may select a patient or subject (e.g., an individual). For example, the user may select the patient or patient identifier through EHR system 110. In response, data exchange system 200 and/or subject identification system 220 (e.g., via an identifier mapping function) may identify the subject identifier associated with the patient identifier and/or in which studies or trials the subject is enrolled and/or participating. As another example, rather than entering information through EHR system 110, the user may select the subject or subject identifier through EDC system 120. In response, data exchange system 200 and/or subject identification system 220 (e.g., via an identifier mapping function) may identify the patient identifier associated with the subject identifier and/or in which studies or trials the subject is enrolled and/or participating. The user may select from such studies and/or trials. If the patient is not registered with a desired study or trial, the user may register the patient (step 506), for example, by providing required information, such as the patient's name or other personally-identifying information (e.g., sex and birthdate), patient identifier, subject identifier, a disease the subject has, current or past treatment, or any other information. A patient or subject may be enrolled in more than one study/trial.

In response to data exchange system 200 receiving an input signal from the user's selections indicating the desired aspects or characteristics of the sought health information, as discussed herein, data exchange system 200 may create a health data query and obtain the EHR data related thereto. The user may be presented with a confirmation request on display screen 152 or web client 150, for example, to confirm the relevance of EHR data obtained in response to the health data query (e.g., in response to a data point obtained being one predetermined to need confirmation). The user may confirm the relevance of obtained EHR data by selecting an input device which transmits an input signal to data exchange system 200 indicating the user's relevance determination.

In response to determining the relevance of obtained EHR data, data exchange system 200 may produce EDC clinical data from the EHR data, and present the same to the user such that the user receives the EDC clinical data in the final standardized data set (step 508). Presentation of the EDC clinical data to the user may be simply for user review and/or reference, and/or for confirmation (step 510), as discussed herein.

Systems, methods and computer program products are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, "satisfy", "meet", "match", "associated with" or similar phrases may include an identical match, a partial match, meeting certain criteria, matching a subset of data, a correlation, satisfying certain criteria, a correspondence, an association, an algorithmic relationship and/or the like.

Terms and phrases similar to "associate" and/or "associating" may include tagging, flagging, correlating, using a look-up table or any other method or system for indicating or creating a relationship between elements, such as, for example, (i) a patient identifier and (ii) a subject identifier, or (i) a data characteristic and (ii) EHR data or EDC clinical data. Moreover, the associating may occur at any point, in response to any suitable action, event, or period of time. The associating may occur at pre-determined intervals, periodic, randomly, once, more than once, or in response to a suitable request or action. Any of the information may be distributed and/or accessed via a software enabled link, wherein the link may be sent via an email, text, post, social network input and/or any other method known in the art.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT, VBScript, Macromedia Cold Fusion, COBOL, MICROSOFT® Active Server Pages, assembly, PERL, PHP, awk, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "JAVA® Cryptography" by Jonathan Knudson, published by O'Reilly & Associates (1998); (3) "Cryptography & Network Security: Principles & Practice" by William Stallings, published by Prentice Hall; all of which are hereby incorporated by reference.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., WINDOWS®, OS2, UNIX®, LINUX®, SOLARIS®, MacOS, etc.) as well as various conventional support software and drivers typically associated with computers.

The present system or any part(s) or function(s) thereof may be implemented using hardware, software or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations or any of the operations may be conducted or enhanced by Artificial Intelligence (AI) or Machine Learning. Useful machines for performing the various embodiments include general purpose digital computers or similar devices.

In fact, in various embodiments, the embodiments are directed toward one or more computer systems capable of carrying out the functionality described herein. The computer system includes one or more processors, such as processor. The processor is connected to a communication infrastructure (e.g., a communications bus, cross-over bar, or network). Various software embodiments are described in terms of this exemplary computer system. After reading this description, it will become apparent to a person skilled in the relevant art(s) how to implement various embodiments using other computer systems and/or architectures. Computer system can include a display interface that forwards graphics, text, and other data from the communication infrastructure (or from a frame buffer not shown) for display on a di splay unit.

As used herein an "identifier" may be any suitable identifier that uniquely identifies something such as a user profile, information, or the like.

As will be appreciated by one of ordinary skill in the art, the system or any of its components may be embodied as a customization of an existing system, an add-on product, a processing apparatus executing upgraded software, a standalone system, a distributed system, a method, a data processing system, a device for data processing, and/or a computer program product. Accordingly, any portion of the system or a module may take the form of a processing apparatus executing code, an internet-based embodiment, an entirely hardware embodiment, or an embodiment combining aspects of the internet, software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general-purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS®, webpages, websites, web forms, prompts, etc. Practitioners will appreciate that the illustrated steps described herein may comprise in any number of configurations including the use of WINDOWS®, webpages, web forms, popup WINDOWS®, prompts and the like. It should be further appreciated that the multiple steps as illustrated and described may be combined into single webpages and/or WINDOWS® but have been expanded for the sake of simplicity. In other cases, steps illustrated and described as single process steps may be separated into multiple webpages and/or WINDOWS® but have been combined for simplicity.

As used herein, "transmit" may include sending electronic data from one system component to another over a network connection. Additionally, as used herein, "data" or "information" may include encompassing information such as commands, queries, files, data for storage, and the like in digital or any other form.

As used herein, the term "network" includes any cloud, cloud computing system or electronic communications system or method which incorporates hardware and/or software components. Communication among the parties may be accomplished through any suitable communication channels, such as, for example, a telephone network, an extranet, an intranet, Internet, point of interaction device (point of sale device, personal digital assistant (e.g., IPHONE®, BLACKBERRY®), cellular phone, kiosk, etc.), online communications, satellite communications, off-line communications, wireless communications, transponder communications, local area network (LAN), wide area network (WAN), virtual private network (VPN), networked or linked devices, keyboard, mouse and/or any suitable communication or data input modality. Moreover, although the system is frequently described herein as being implemented with TCP/IP communications protocols, the system may also be implemented using IPX, APPLE®talk, IP-6, NetBIOS®, OSI, any tunneling protocol (e.g. IPsec, SSH), or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA® 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish Networks®, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method for producing an electronic data collection (EDC) standardized data set, the method comprising:
receiving, by a processor, a request for relevant subject health information including a subject identifier from an electronic data collection (EDC) system, the subject identifier associated with a subject for a clinical trial, the subject including at least one of an individual, a disease, a medical topic, and a treatment;
matching, by the processor, the subject identifier associated with the subject to a patient identifier in an electronic health record (EHR) system, wherein:

the subject identifier was previously generated in response to the subject being entered into the EDC system, the subject identifier being unique for the subject, and the subject identifier and the patient identifier were previously mapped together as being associated, by the processor, in response to the subject being entered into the EDC system;

transmitting, by the processor, a health data query comprising the patient identifier to at least one of the EHR system or a data transfer application programming interface to obtain EHR data associated with the subject;

receiving, by the processor, the EHR data associated with the patient identifier;

parsing, by the processor, the EHR data into relevant EHR data and nonrelevant EHR data, wherein the parsing the EHR data comprises reviewing the EHR data for a relevance indicator comprised in electronic health record (EHR) data points of the EHR data, and separating the EHR data points comprising the relevance indicator from the EHR data points missing the relevance indicator;

displaying, by the processor, a first data set of the relevant EHR data on a user interface of a user device requesting a first confirmation by a user that the first data set of the relevant EHR data is at least one of relevant or irrelevant, the first data set corresponding to a first group of data from a first medical visit within a predetermined time period;

displaying, by the processor, a second data set of the relevant EHR data on the user interface of the user device requesting a second confirmation by the user that the second data set of the relevant EHR data is at least one of relevant or irrelevant, the second data set corresponding to a second group of data from a second medical visit, within the predetermined time period; subsequently receiving, by the processor, at least one of the first confirmation and the second confirmation from the user through the user interface of the user device; subsequently applying, by the processor, an electronic data collection (EDC) mapping function to the relevant EHR data; and producing, by the processor, an electronic data collection (EDC) clinical data in a final standardized data set usable in the EDC system in response to the applying the EDC mapping function to the relevant EHR data.

2. The method of claim 1, wherein the health data query to the EHR system comprises a data characteristic indicating the EHR data, and wherein the received EHR data associated with the patient identifier comprises the data characteristic.

3. The method of claim 1, wherein the EDC mapping function transforms the relevant EHR data into the EDC clinical data.

4. The method of claim 3, wherein the applying the EDC mapping function to the relevant EHR data comprises analyzing and transforming the relevant EHR data to the EDC clinical data.

5. The method of claim 4, wherein the applying the EDC mapping function to the relevant EHR data further comprises removing the relevant EHR data not pertinent to the clinical trial.

6. The method of claim 4, further comprising applying, by the processor, a data mapping function to a data category in the received EHR data to associate the data category in the received EHR data with a corresponding data category in the final standardized data set before the parsing the EHR data occurs.

7. The method of claim 1, further comprising confirming, by the processor, at least one of relevance of the relevant EHR data or accuracy of the produced EDC clinical data.

8. The method of claim 1, further comprising presenting, by the processor, the EDC clinical data on a user interface requesting confirmation by the user that the produced EDC clinical data is accurate.

9. The method of claim 8, further comprising receiving, by the processor, a confirmation response indicating whether the EDC clinical data is accurate, and in response to the confirmation response indicating that the EDC clinical data is not accurate, adjusting, by the processor, the EDC mapping function and reapplying the EDC mapping function to the relevant EHR data.

10. The method of claim 1, wherein the EHR data received is transformed raw data comprising a structured format.

11. A system, comprising:
a display screen comprising a web client with a graphical user interface (GUI); and
a data exchange system comprising a server, the data exchange system configured to provide the GUI through the web client, the data exchange system comprising:
a processor;
a tangible, non-transitory memory configured to communicate with the processor, the tangible, non-transitory memory having instructions stored thereon that, in response to execution by the processor, cause the processor to perform operations comprising:
receiving, by the processor, a request for relevant subject health information including a subject identifier from an electronic data collection (EDC) system, the subject identifier associated with a subject for a clinical trial, the subject including at least one of an individual, a disease, a medical topic, and a treatment;
matching, by the processor, the subject identifier associated with the subject to a patient identifier in an electronic health record (EHR) system, wherein:
the subject identifier was previously generated in response to the subject being entered into the EDC system, the subject identifier being unique for the subject, and
the subject identifier and the patient identifier were previously mapped together as being associated, by the processor, in response to the subject being entered into the EDC system;
transmitting, by the processor, a health data query comprising the patient identifier to at least one of the EHR system or a data transfer application programming interface to obtain EHR data associated with the subject;
receiving, by the processor, the EHR data associated with the patient identifier;
parsing, by the processor, the EHR data into relevant EHR data and nonrelevant EHR data, wherein the parsing the EHR data comprises reviewing the EHR data for a relevance indicator comprised in electronic health record (EHR) data points of the EHR data, and separating the EHR data points comprising the relevance indicator from the EHR data points missing the relevance indicator;

displaying, by the processor, a first data set of the relevant EHR data on a user interface of a user device requesting a first confirmation by a user that the first data set of the relevant EHR data is at least one of relevant or irrelevant, the first data set corresponding to a first group of data from a first medical visit within a predetermined time period;

displaying, by the processor, a second data set of the relevant EHR data on the user interface of the user device requesting a second confirmation by the user that the second data set of the relevant EHR data is at least one of relevant or irrelevant, the second data set corresponding to a second group of data from a second medical visit within the predetermined time period; subsequently receiving, by the processor, the first confirmation and the second confirmation from the user through the user interface of the user device;

applying, by the processor, an electronic data collection (EDC) mapping function to the relevant EHR data; and producing, by the processor, an electronic data collection (EDC) clinical data in a final standardized data set usable in the EDC system in response to the applying the EDC mapping function to the relevant EHR data; and storing, by the processor, the EDC clinical data and the subject identifier in the final standardized data set.

12. The system of claim 11, wherein the health data query to the EHR system comprises a data characteristic indicating the EHR data, and wherein the received EHR data associated with the patient identifier comprises the data characteristic.

13. The system of claim 11, wherein the EDC mapping function transforms the relevant EHR data into the EDC clinical data.

14. The system of claim 13, wherein the applying the EDC mapping function to the relevant EHR data comprises analyzing and transforming the relevant EHR data to the EDC clinical data.

15. The system of claim 14, wherein the applying the EDC mapping function to the relevant EHR data further comprises removing the relevant EHR data not pertinent to the clinical trial.

16. The system of claim 11, wherein the operations further comprise presenting, by the processor, the relevant EHR data on a user interface requesting confirmation by a user that the relevant EHR data is relevant before applying the EDC mapping function.

17. The system of claim 11, wherein the operations further comprise confirming, by the processor, at least one of relevance of the relevant EHR data or accuracy of the produced EDC clinical data.

* * * * *